United States Patent [19]
Cosman

[11] Patent Number: 6,143,003
[45] Date of Patent: *Nov. 7, 2000

[54] REPOSITIONER FOR HEAD, NECK, AND BODY

[76] Inventor: Eric R. Cosman, 872 Concord Ave., Belmont, Mass. 02178

[*] Notice: This patent is subject to a terminal disclaimer.

[21] Appl. No.: 08/736,495

[22] Filed: Oct. 24, 1996

Related U.S. Application Data

[63] Continuation-in-part of application No. 08/382,226, Jan. 31, 1995, abandoned.
[51] Int. Cl.$^7$ .................................................. A61B 19/00
[52] U.S. Cl. ............................................ 606/130; 128/846
[58] Field of Search .................................. 606/130–236; 128/866, 846

[56] References Cited

U.S. PATENT DOCUMENTS

4,618,978 10/1986 Cosman .................................. 606/130
5,464,411 11/1995 Schulte et al. ......................... 606/130
5,531,229 7/1996 Dean et al. .............................. 606/130

*Primary Examiner*—Michael Buiz
*Assistant Examiner*—Kevin Truong
*Attorney, Agent, or Firm*—Darby & Darby P.C.

[57] ABSTRACT

For repeat localization and immobilization of the head, neck and/or torso of a patient's body, immobilizing structures are used to secure the head and the neck and torso in a relative orientation in the position and relative orientation. A reference structure determines the relative position of the head and neck or torso so that the same configuration of these portions of the body can be achieved on a scanner couch or treatment machine couch repeatedly. Several forms of head and neck or torso immobilizers accommodate specific objectives and several forms of reference structures accomplish repositioning and patient position orientation.

18 Claims, 4 Drawing Sheets

REPOSITIONER FOR HEAD, NECK, AND BODY

This is a continuation-in-part of U.S. patent application, Ser. No. 08/382,226 filed Jan. 31, 1995 now abandoned by Eric R. Cosman for "A Head and Neck Localizer."

BACKGROUND AND SUMMARY OF THE INVENTION

In the above-mentioned parent patent application, a patient immobilizer and localizer was described which is suitable for image scanning and for positioning on a treatment table, such as a linear accelerator (LINAC). Various embodiments of the invention were described therein including an over-arm structure oriented in the quasi-sagittal plane of the patient which immobilizes the head by, for example, a dental impression with biasing straps to apply pressure on the upper teeth, an occipital form, various external molded forms, etc. Various types of graphic reference structures to index tomographic scanning through the patient with the immobilizer in place were described and various target and therapeutic beam localizing structures were described to align internal targets determined from scanning to the convergence or path of external beams or other probes or instruments to the patient's head, neck, and upper thorax regions.

In general, the system and method of the present invention is directed to further examples, embodiments, and improvements of the foregoing patent application. Further examples of patient immobilizer structures are given. A reference structure is shown which enables the repeat orientation and positioning of the head relative to the neck, spine, and upper thorax. Further examples of graphic reference structures for image scanning and target and beam localization structures for therapy or other interventions are described.

BRIEF DESCRIPTIONS OF THE DRAWINGS

In the drawings which constitute a part of the specification, exemplary embodiments exhibiting various objectives and features hereof are set forth, specifically.

DESCRIPTION OF THE INVENTION

The following embodiments illustrate and exemplify the present invention and concepts thereof, yet in that regard, they are deemed to afford the best embodiments for the purpose of disclosure and to provide a basis for the claims herein which define the scope of the present invention.

Figure 1:
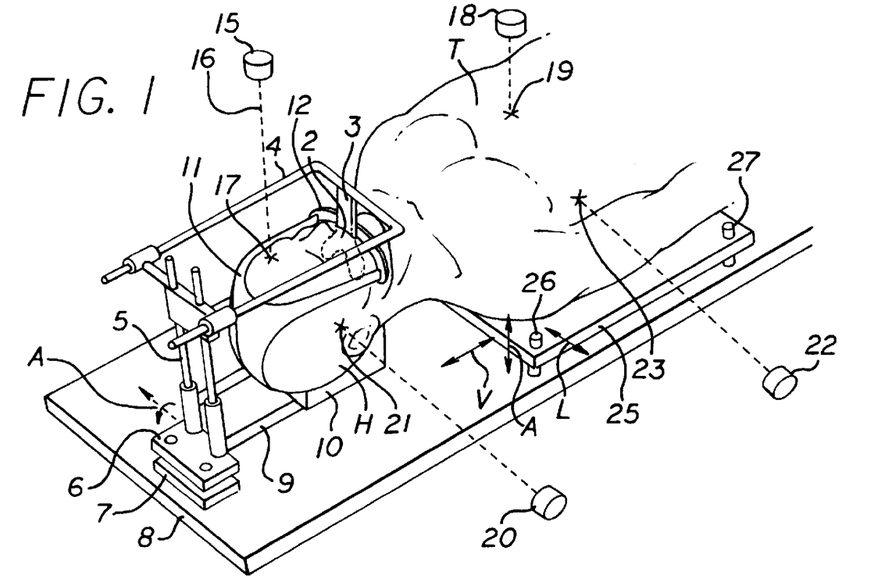
FIG. 1 is a diagram of a head immobilizer and a translation system for repositioning of the torso relative to the head in accordance with the present invention.

Referring to FIG. 1, the patient's head H is immobilized by several elements. A dental tray 2 is in the mouth and an impression of the upper dentition and/or the lower dentition can be made. The dental plate is connected by element 3 to an over-arm structure 4 which is fastened by further vertical structures 5 to the base form 6 and sub-plate 7, which is attached to the couch 8. Further structures 9 secure an impression or cushion 10 for the back portion of the patient's head. A biasing strap 11 is secured to the dental tray portion by an attachment device 12 which provides a biasing force of the dental tray to the upper teeth of the patient and supplies a securing force of the patient's head H to the cushion 10. The patient's head H is thus immobilized and can be repositioned in the same orientation. The plate 6 may be tilted about axis A for orientation of the patient's head in the event of sag of the table 8 or in the event of sag of any of the structures such as 5, 4, etc. It may be desirable to orient the torso or upper shoulders T of the patient relative to the patient's head in the same position during CT or MRI image scanning as when the patient is repositioned on a treatment couch such as for a LINAC X-ray treatment machine. In this sense, the position, orientation, and articulation of the torso T can be variable relative to the head H under unconstrained conditions. Thus, to align and position the torso T relative to the head in an identical position as in repositioning on a treatment couch for multiple fractionated treatments over many sessions, a referencing of the torso T relative to the head can be made. The torso may be laid on a flat table whose elevation is known relative to cushion 10 and dental form 2. If cushions or uncertainties are present during scanning, it is desirable to make quantitative reference measurements of the relative positions of the torso, neck, spine, and head. An example of such referencing is shown in part in FIG. 1. A laser source 15 shines laser beam 16 onto a spot 17 on the patient's head from a vertical orientation. Another laser source 18 shines similarly laser light on another spot 19 on the torso. Similar lasers 20 and 22 shine on markings 21 and 23 on the surface of the patient. The laser beams could be sheets, lines, or cross lines as is common. Lasers 15, 18, 20, and 22 could be on a fixed mechanical structure which can be placed and aligned relative to couch 8. Or the lasers may be displaced on a track or sliding system such that 15 may be slid to position 18 for the purpose of aligning to marks 17 and 19, and similarly could be done for sliding laser 20 to position of laser 22 in FIG. 1. In this way, the laser referencing structure could be implemented at the time of CT scanning, and the markings 17, 19, 21, and 23 could be put onto the patient's body. At the time of treatment, a similar laser reference system could be put into place, and the laser beams from the respective lasers made to align to the surface markings on the patient 17, 21, 19, and 23 by articulation and movement, for example, of the torso T relative to the head H. The position of the head H can also be moved by translation structures in elements 4, 5, etc. Or, the torso T may be moved by a translation of, for example, a sub-table 25 which can move in the lateral direction L, the AP direction A, or the vertical direction V, indicated by the arrows, with reference to the patient's coordinates. Thus the torso can be translated and trammed in by, for example, the jack screws 26 and 27 and similar jack screws on the opposite side of the patient not shown. The tilt of the patient's torso could also be manipulated in pitch, roll, and yaw angles, for example, of the platform 25 by adjustment screws. In this way, the skin mark 19 and 23 on the torso, for example, could be brought into relative alignment with respect to the lasers 18 and 19, they being in a relatively known position with respect to lasers 15 and 20 and their respective skin marks 17 and 21. This illustrates a way of orienting the otherwise multiple-degree-of-freedom orientation of torso and neck with respect to an immobilized head.

Figure 2:
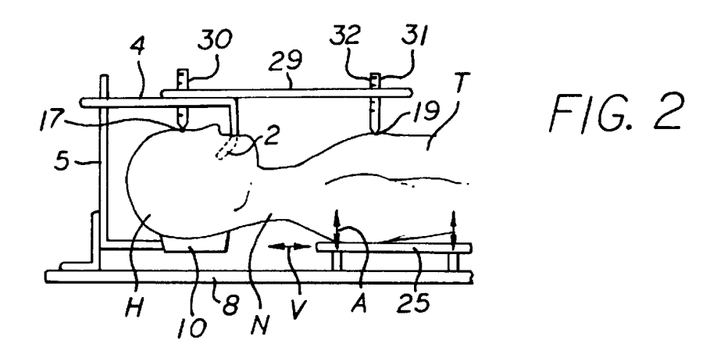
FIG. 2 is a schematic elevation view illustrating an embodiment of the present invention with a mechanical referencing structure and shoulder positioning structure for repeat localizing.

FIG. 2, in accordance with the present invention, illustrates an elevation view of the head H with cushion structure 10 and over-arm structure 5 and bar 4 with dental piece 2, similar to FIG. 1. The treatment or scanning couch 8 is shown, and a sub-plate 25 is illustrated with the same possibility of translation and rotations as described for FIG. 1. In addition, a reference structure 29 is shown attached to over-arm element 4. It has depth probes 30 and 31 which can determine the distance to positions 17 and 19 on the patient's head and torso, respectively. The depth rods 30 and 31 may have scales on them, such as 32, to illustrate the depth from the upper surface of reference structure 29. Thus, when the patient's head H is positioned repeatedly by means of the dental impression 2 and cushion 10, the torso T, and therefore the upper shoulders and neck, can be appropriately positioned in a repeat orientation to the head H by the reference structure 29 by bringing into alignment via the depth probes 30 and 31 a predetermined position or marking 19 on the chest relative to a predetermined marking or position 17 on the head. Many such markings as 17 and 19 could be made at various positions of the head H, the neck N, and the torso T so that a considerable amount of geometric data can be taken of the relative orientation and articulation of the body portion from head to torso. If needed, the torso could be translated relative to the head by, for example, anterior-posterior movements A, lateral movements L (not shown), or vertical movements V of the table 25 so as to bring the points 17 and 19 into appropriate relative alignment via the reference structure 29. In this way, a patient's head and neck and upper torso can be brought into a repeat similar alignment for one episode after another on a scanning or treatment couch.

Figure 3:
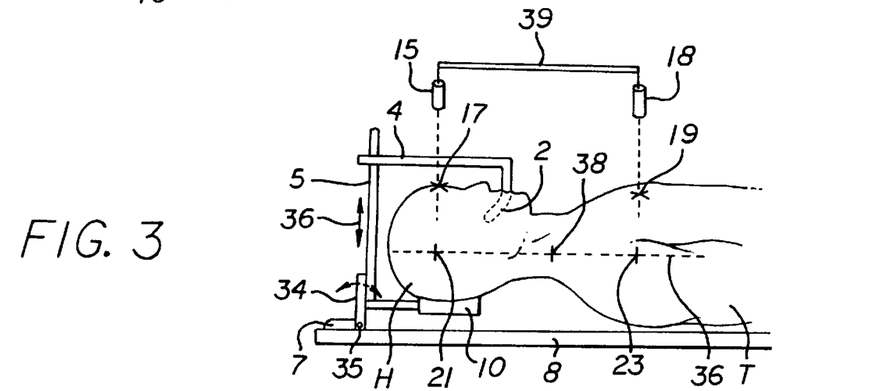
FIG. 3 shows an alternative embodiment with further reference structures and translation devices.

According to the present invention, FIG. 3 shows an alternative embodiment of a head immobilizer together with a referencing structure to reposition identically the articulation of the neck and/or shoulders relative to the head. As in the above example, the head H is positioned by occipital cushion 10 and over-arm structures 4 and 5 plus the dental impression or bite piece 2. Piece 2 may be of different shapes depending on the degree of opening or closure of the mouth, and in accordance with the type of treatment needed. For example, treatment of cancer of the mouth, tongue, jaw, and neck may require differing degrees of mouth opening or jaw position and, for example, the mouth element 2 could have larger or smaller widths to accommodate such positions. Furthermore, the clamp mechanism to the couch 8 might have a base portion 7 and a clamp portion 34 which can rotate on pivot 35 so as to change the angulation of the entire head orientation for proper alignment, for example to laser lights on a scanner or treatment couch. Furthermore, the position of the head can be varied by translation such as movement 36 in the vertical so as to appropriately align the head to horizontal lasers relative to the treatment couch. Horizontal lasers, for example, could cast a dashed line such as 36 onto the lateral portion of the patient's body. To reposition the patient in the same articulation, head, neck, and torso, index marks such as 21 and 17 may be present on the lateral and anterior portions of the patient's head or 23 and 19 on the anterior or lateral portions of the patient's neck or torso. Other index marks such as 38 may be present in plurality over the surface of the patient's skin. Laser lights 15 and 18 may be present, and they could be connected rigidly or adjustably by structural element 39. Similar lasers could be pointing in the horizontal direction analogous to 20 and 22 in FIG. 1 to shine upon the body in the lateral aspect. The lower portion of the patient's torso T may rest on the horizontal table 8 and by adjusting the translation of the patient's head, such as axis 36 in the anterior-posterior direction or lateral and vertical axes, the patient's head H can be repositioned in the same orientation as during CT scanning, i.e. the laser lights and spots being aligned with respect to the reference structure 39 which may be a similar reference structure to that used at the time of CT scanning to determine the index points on the skin in the first place. Thus the reference structure 39, in this case being a set of lasers, provides an apparatus to realign the articulation of moveable portions of a patient's body so as to bring those portions of the body into realignment as they were at some previous time. This enables repeated repositioning of the body repeatedly on a treatment couch for the purpose of, for example, irradiating the same target within the body as determined from a CT image.

Figure 4:
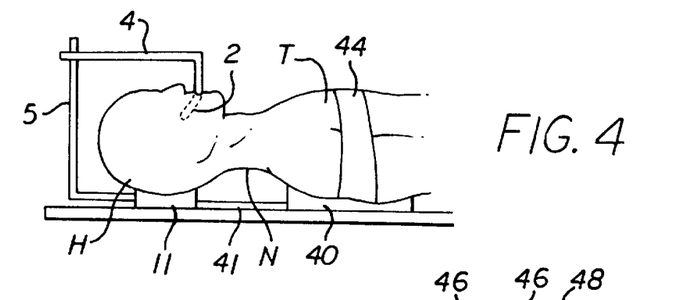
FIG. 4 is an elevation view of an alternative form with patient immobilization of the head and shoulders giving relative reference to each.

In FIG. 4, another embodiment of reference structure can be used for realignment of the patient's head, neck, and upper body. Again, the head H is clamped by posterior cushion 10 and over-arm structures 4 and 5 with dental piece 2. The upper torso T can be oriented with respect to head H by a body mold or cushion 40 which immobilizes or restrains the back portion of the patient's shoulders or neck. A connection 41 may exist between cushion 11 under the head and cushion 40 under the torso so as to bring them into a relatively fixed and repeatable orientation. The head mold 11 and torso or shoulder mold 40 may be one integral body cast or mold and may extend continuously along the contours of the neck between connection 41 may thus be a continuous extension of 11 and 40 and may contour to the neck N of the patient in one full case of the head, neck, shoulders, and torso. Int his case 11, 41, and 40 would be a physical reference structure to align the head, neck, and/or torso in a repeatable fashion on CT scanner and treatment (viz. LINAC) couch. In this way, the patient's body, head, and neck can be brought into repositioning via the reference structure, which in this case is the conjugation of cushions 11 and 40 together with a connection element 41.

Figures 5, 6:
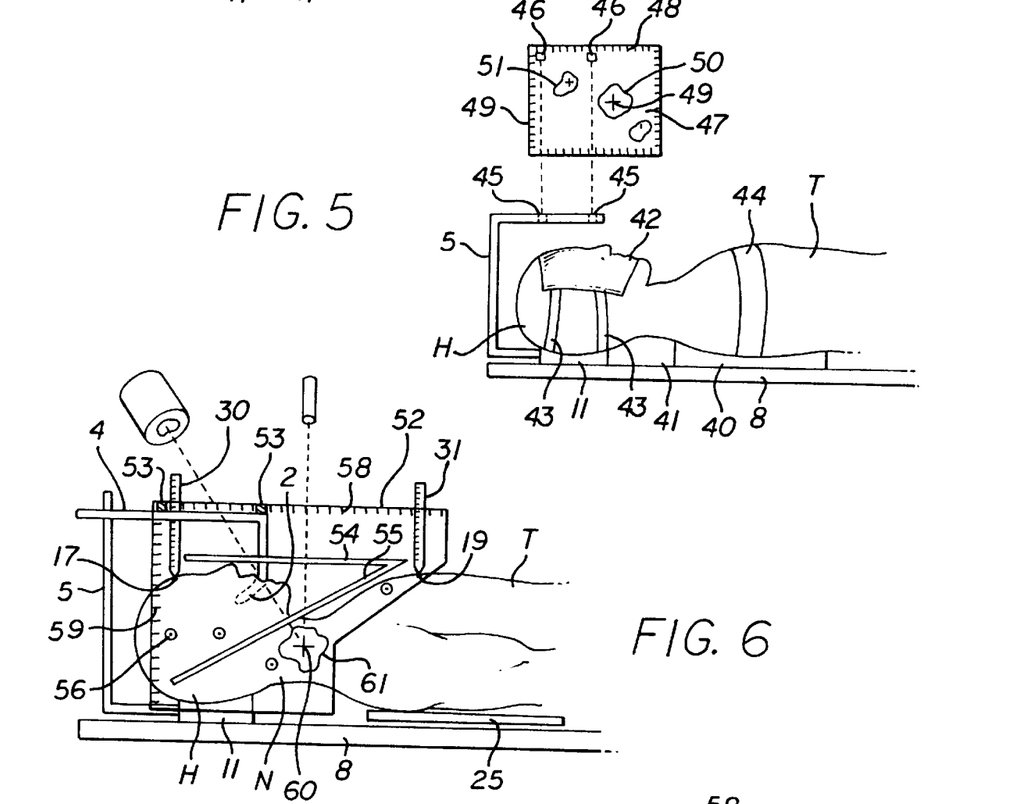
FIG. 5 is an elevation view of another alternative form of the present invention involving surface masks, molds, and target localizers.
FIG. 6 shows an alternative form of the present invention with reference structure and graphic reference structure.

FIG. 5 is yet another example of patient immobilization. In this case, the patient's head H is immobilized by posterior cushion or mold 11, but also by a mask or mold structure 42 which conforms to the external surface of the patient's head H in the front portion. The mask 42 is constrained or secured to the posterior cushion in this example by straps 43, which could be elastic or belt-like structures. Similarly, the upper torso T is restrained by a molded form 40 which, for example, may be a beanbag, vacuum cushion, cast-formed to the patient's body, foam-formed, etc. Also shown is the neck case or mold 41 contouring to the neck region. It may or may not be separate from 11 and/or 40. It may for example be one continuous molded or contoured structure with 11, 41, and 40 forming a single body mold. It would be a reference structure for positioning repeatedly the head, neck, and torso in the same orientation. A restraining belt or form 44 may be used to immobilize the patient's torso, and indeed such immobilizing restraints on the torso or neck could be present in any of the examples above. The over-arm structure 5 in this case has docking holes 45 which accept pin structures 46 in a target referencing structure 47. This referencing structure can have axes 48 and 49 with scales on them to quantitative reference the coordinate system of the patient's head via the connection through the over-arm 5 and the restraint elements 11 and 42. Thus, during CT scanning, a graphic reference structure can be used (see the parent application for examples of this and the coordinates for every physical point on the patient's head determined relative to the over-arm structure 5 and restraint members 11 and 42). Thereafter, a computer workstation may calculate target volumes to be treated by external beam irradiation, and these target positions, shapes, and volumes, as well as beam ports, directions, and shapes can be represented on the sides of the target structure such as 47 such that when that structure is placed on the arm 5 and the patient with this apparatus placed on a treatment couch, the target position such as 49 can be set to the beam axis via laser lights. The target volume or port shape 50 can be described on such a target structure sheet. Beam ports such as 51 with irregular shapes can be described also on these sheets corresponding to radiation beams with conformal collimators being pointed at the target structure within the patient's head. The referencing structure in this case are the cushions 11 and 40, and they may be secured to the couch table 8 in an indexed fashion by pins in the cushions located to the couch or by measured positions of the cushions along the couch so as to reposition the patient in the same orientation and articulation as he was during CT scanning.

FIG. 6 shows aspects of another embodiment of the present invention for head and neck localization and registration relative to the torso. As above, the head cushion 11, arm structure 5 and 6, and mouthpiece 2 are shown. A reference structure 52 is a frame which can be mechanically attached to the over-arm structures, for example by fasteners 53. The reference structure has parallel 54 and diagonal 55 elements which are radiopaque and can be seen in CT scanning. They may also have MRI visibility for MRI scanning. The patient may be placed upon a CT scanner couch 8, and depth probes 30 and 31 may pass through holes in reference structure 52 at known positions, and they may be made to point to physical spots 17 and 19, for example, on the patient's body surface. Many more spots may be present, and many more depth probe holes from the top or laterally (such as hole 56 and others) may be present. By passing the depth rods such as 31 to the patient's skin and making an ink mark at 17 for all or selected rod holes, the orientation of the patient's body, head H, neck N, and torso T, may be "calibrated" or determined relative to the reference structure. A CT scan may proceed, and the index rods and diagonals 54 and 55, which may be on the sides and top of the reference structure and also on the bottom in some cases, to index the scans and all the scan data relative to the reference structure. Also included in the CT scan data is the patient's anatomical image data, which again is referenced to the reference structure 52. Subsequently, after scanning, if the patient treatment plan is developed on a treatment planning computer in which the scan data with the reference indicia from index structures 54 and 55 are computed in the computer, the anatomical data of the patient's body can be referenced to the coordinate system represented by reference structure 52 with its orthogonal scales 58, and 59. Similar scales can be on the top (anterior) and other side of the reference structure. Thus, each pixel in the image data of the anatomy in the head, neck, and torso can be registered relative to the coordinate system of the reference structure 52. Thus, a target 60, which is determined in the neck, for example, or a target volume 61, as seen in projection in FIG. 6, can be determined from the treatment planning process and its position on orthogonal projection can be indicated on the side plates of the reference structure 52. Overlay sheets may be used for this purpose or computer-generated sheets may be laid upon the reference structure to indicate these positions. When the patient is placed upon the treatment couch, his head H and torso T can be brought into the same orientation relative to the reference structure 58 by placing the sounding rods 30, 31, and others (for example through holes like 56) so as to bring the markers 17 and 19 to the same position and depth as read on the scales for the rods 30 and 31, etc., thus qualifying that for a number of surface points the patient has been brought into the same orientation to the reference structure 52 as he was during the CT scanning. Thus the reference structure 52 acts as a base frame with respect to which the patient's body with its various articulations can be brought repeatedly into registration by quantifying reference points on the patient's body relative to the reference structure, as illustrated above. In this way, repeat localization of a patient's body relative to the reference structure can be achieved. This may require moving the patient's body or various parts of the body on the table, or by having sub-plates such as 25 on the table so as to translate in three axes or create angular orientations of the torso T and neck N relative to the head.

Figure 7:
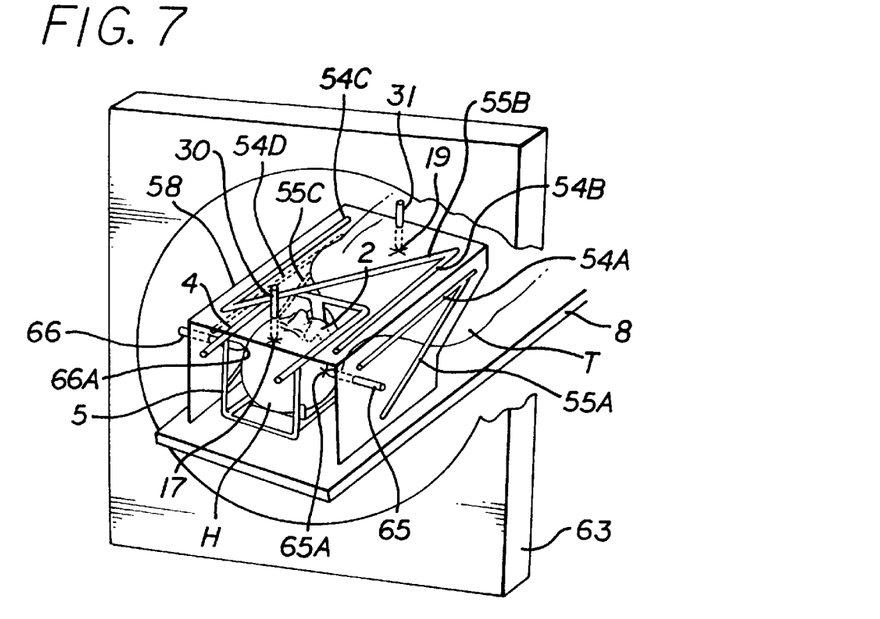
FIG. 7 shows a form of the present invention with a tomographic reference structure in place.
Figure 8:
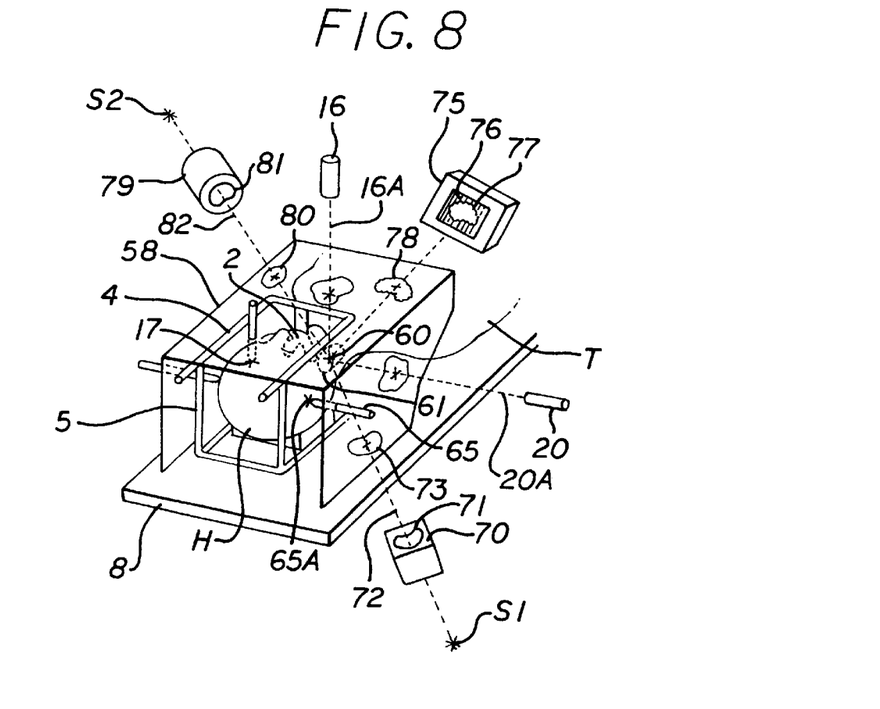
FIG. 8 shows an extension of the form of FIG. 7 during treatment on an X-ray delivery system with target/beam reference structure.

In combination, FIGS. 7 and 8 illustrate a process and system by which this registration and re-registration from scanning to treatment phase is illustrated. In FIG. 7, a CT or MR scanning machine 63 is illustrated. The scanner table is illustrated by 8, and the patient's head H and torso T are on the table. Over-arm structure such as 5 and 4 are shown analogously to the examples above including the dental piece 2. Diagonal graphic structure elements 55A, 55B, and 55C are shown on the sides and top of the structure, and similarly parallel rods 54A, 54B, 54C, and 54D are shown. It is known from the work of R. Brown (U.S. Pat. No. 4,608,977) that such diagonal structures can index the anatomical data of the scan relative to the reference structure 58. In addition, depth rods 30, 31, 65, 66, and others (not shown) are illustrated to index to surface points on the patient's skin 65A, 19, 17, 66A, etc., corresponding to each of the depth rods. These index points can be marked at the time the patient is on the table or at a previous time at the clinician's convenience. Thus the orientation of the body relative to the reference structure 58 is determined. Furthermore, the reference structure 58 can be aligned by laser beams associated with the scanner 63, if desired, so that therefore the patient's body is in a known reference to laser lights associated with the scanning machine.

In FIG. 8, a similar geometry reference structure, or perhaps the exact same reference structure, 58 is shown over the patient's body where similar alphanumerics indicate similar objects as in the previous figures. Again, the depth rods such as 65 point to the same reference markers such as 65A, 17, etc. on the patient's skin (others of the depth rods are not shown for simplicity). A target 60 determined from treatment planning within the patient's body and target volume V illustrated by the dashed line are shown/this may be for example a tumor in the cranium, skull base, nasopharynx, jaw, tongue, neck, upper torso, lymph nodes, etc., as detected from CT data in stereotactic frame coordinates from the examples of FIG. 7. The target 61 may be positioned so that its center 60 lies at the isocenter of radiation beams from, for example, a LINAC. This isocenter is typically located by laser beams such as 20A from laser 20 and 16A from laser 16, which can be pre-set along the cardinal axes towards isocenter. From the treatment planning computer and CT scan data derived from scanning as in FIG. 7, beam ports can be determined with contoured or circular shapes. For example, a contoured block 70 with contoured beam port shape 71 sends a beam of that shape along a line 72 from X-ray or field light source S1 to radiate the target volume 61. The beam's projection 73 may be marked on the side plate of the reference structure 58. This may be done by computer calculation or it may be marked by a quality assurance pre-run of the treatment on the LINAC machine or a LINAC simulating machine. Another type of collimator is shown as 75, which is a multileaf collimator having multiple high density leaves 76 to give a beam shape 77 for an irradiation source. The projection of that beam shape may be illustrated as 78 cast upon the top surface of reference 58. Another port or collimator 79 is shown, and also shown is source 52, which may be the X-ray irradiation source of a LINAC or it may be the light source corresponding to "field lights" in such LINACs. The X-ray beam, and therefore field lights, will cast a projection 80 onto the top surface of the localizer. This projection 80 can serve as a quality assurance check that the correct collimator shape, such as 81, is projected from the correct direction, illustrated by dashed line 82 towards the target volume 61.

As illustrated in FIGS. 7 and 8, the reference structure 58 acts as the intermediary structure to relocate the patient's head, neck, and torso in the same configuration on an analogous couch 8 in each figure, that in FIG. 7 being the CT scanning couch; and that in FIG. 8 being the treatment couch for a LINAC. Once this co-registration of the patient's body to the reference structure 58 has been done, then targets seen from CT scanning as calculated from treatment planning can be determined in physical space of the reference structure, and the targets in turn can be located at a physical point such as isocenter of a linear accelerator and the geometry of beam configurations can be quantitatively determined in the coordinate reference system of the reference structure 58. The patient's body may be moved in a variety of ways including sliding the body along the table, putting cushions under the body, having elevating or angulating sub-platforms such as 25 in FIG. 6, etc. to bring the index marks on the skin into correct alignment relative to the reference structure for the repositioning operation.

Figure 9:
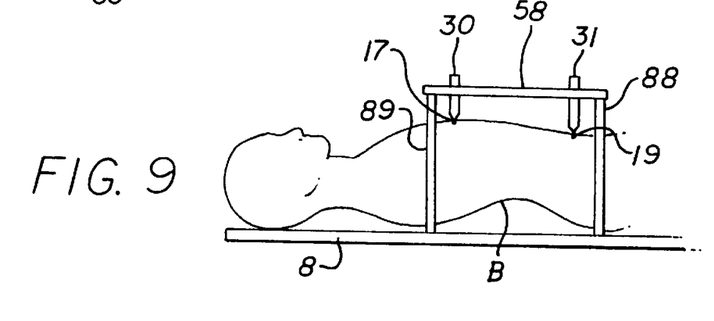
FIG. 9 shows an extension from the head and neck to the body with an alternative form of the present invention.

FIG. 9 shows an embodiment of the invention in the form of a reference structure 58, the body B of the patient. The body portion B may be the thorax, lower abdomen, pelvis, or the head and neck. Depth rods 30 and 31 point to reference points on the patient 17 and 19 similar to the discussion above. Similar depth rods can be present on the lateral aspects of the reference structure 58 (not shown). The reference structure 58 can be positioned relative to the treatment or scan couch 8 by reference elements 88 and 89, which may be mechanical attachments to prefixed positions or could be positioned, for example, by remote devices such as optical registration, ultrasonic registration, etc. The reference structure as in FIG. 8 and FIG. 9 can be aligned by laser lights such as 20 and 16 to the treatment planning machine or to the couch 8. These laser lights are common in treatment planning machines, and thus the coordinate reference of the reference structure 58 can be brought into co-alignment and registration of the coordinate system associated with the treatment planning machine. In turn the patient's body is brought into said pre-alignment with the machine, and the target structures can thereby be determined at isocenter and in the volumetric space of the treatment machine.

Figure 10:
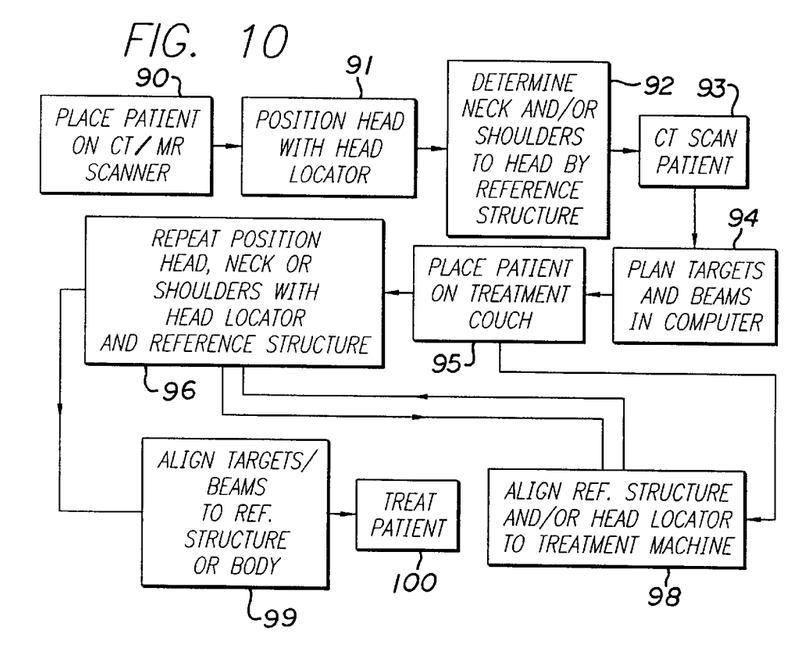
FIG. 10 shows a process diagram in accordance with the present invention.

Referring to FIG. 10, a process block diagram is shown in accordance with the present invention. This illustrates one sequence of events that is possible to register and re-register the patient from scanner to treatment machine, as an example. In the first phase, block 90 indicates placement of the patient in the CT or MRI scanner. The patient's head may be pre-set prior to step 90 by putting on the head locator; or the head locator may be placed on the patient once he is on the scanner couch. The step of placing the head locator immobilizer is block 91. Such an immobilizer might be a bite piece or mask structure on his head, as shown in the above examples. The next step 92 would be to determine the position of the shoulders and neck relative to the head and determine that registration relative to a reference structure as in the discussion above. This procedure of referencing to a reference structure could have been done prior to placing the patient on the scanner couch, or it could have been done during the session 90 on the scanner couch. The position of the shoulders, upper torso, and neck are recorded relative to the head position or reference data is taken associated with the articulation of the shoulders relative to the head, as illustrated by the examples above. This might involve skin markings, depth probing, molds of the shoulders and neck relative to the head, etc. Once the shoulders and head are in registration or their position has been recorded relative to each other, the scan of the patient can take place, indicated by element 93. The image scan data can be taken with reference markers or graphic reference structure index data, or simply the slice indexing of the scanner itself with pixel data within each slice may be downloaded to a computer workstation where a treatment plan is done, indicated by block 94. Treatment planning computers are illustrated by the XKnife workstation of Radionics, Inc., Burlington, Mass. Calculation of target, target coordinates, Beam's-Eye View of targets, beam or port configurations, and beam angles are among the outputs of such a treatment planning calculation, indicated by 94. Later (of if the CT scanner is integrated with the treatment machine, simultaneously), the patient is placed on the couch of the treatment machine such as a LINAC, indicated by step 95. Steps 96 and 98 can be done in any order or essentially at the same time wherein 96 indicates the repositioning of the head, neck, and shoulders relative to the reference structure frame of reference as indicated in blocks 91 and 92 for the CT scanner. The reference structure may be aligned relative to the laser lights of the LINAC or otherwise to the treatment planning coordinate frame, indicated by block 98. Step 98 may have been done prior to step 96, or in the inverse sequence, step 96 could be done and then the patient may be brought into alignment to the coordinate frame of the reference structure, and the reference structure into alignment with the coordinate system of the treatment machine 98. The reference structure information as determined by step 92, which may involve angle, depth, and position data or markings on the skin, etc. can be used during the steps 96 and 98 to coordinate the position of the patient's anatomy to the treatment machine. Next, the target determined from the treatment planning process 94 can be determined relative to the reference structure or marked, for example, on the reference structure. These markings, coordinate settings, or referencing data can be used to align the beams of the treatment machine to the reference structure and/or the body, as shown in step 99. This may involve marking the target position on laser projection markings, such as on the reference box described above; it may involve setting a coordinate on a target scale which may be part of the reference structure shown above; it may involve setting laser lights from the treatment machine indicative of isocenter, for example, on markings on the patient's body as data from the referencing structure, as described above. The description, shape, or orientation of beam ports may also be described on the reference structure, drawn thereon, or computer simulations of said beam geometries and ports overlaid on the box structure by transfer sheets so as to give information on the beam directions and their proper orientations and configurations. Once step 99 is complete, the patient can be treated appropriately in step 100 under beams from the radiation machine.

Figure 11:
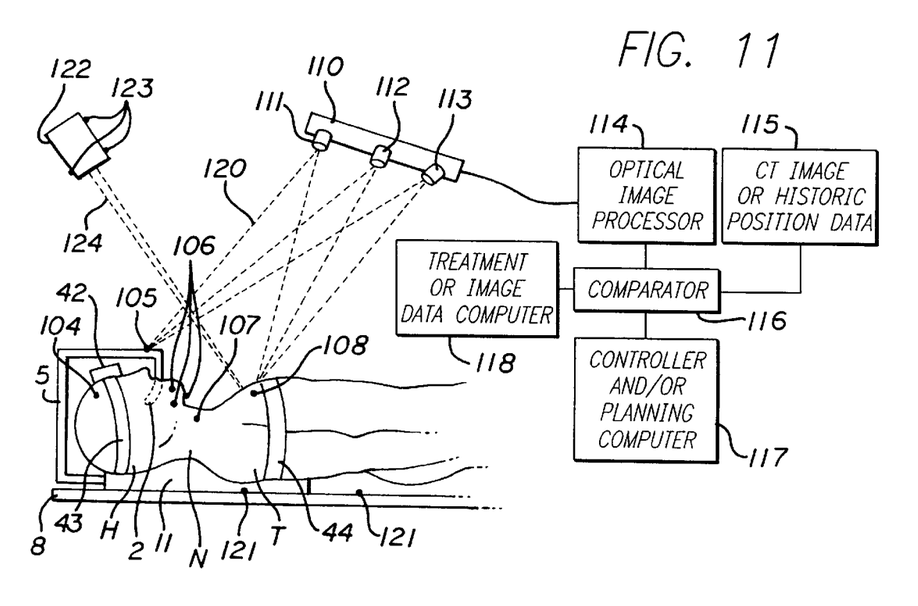
FIG. 11 is another embodiment according to the present invention.

Referring to FIG. 11, another embodiment according to the present invention is shown. Again, a CT scanner or treatment machine couch 8 supports the patient's body. Contour structure 11 is contoured to the head, neck, and upper shoulder or upper torso. Another contour element 42 on the patient's head is in place, and securing strap 43 to the base 11 secures the head in a position, predetermined or determinable. A restraining strap 44 immobilizes and restrains the upper torso to the contour of mold 11. Alternatively, or in addition, a dental piece 2 could be in place to further fixate the head in a position. It is supported by over-arm structure 5, which for head and neck treatment beams is in a sagittal or quasi-sagittal configuration so as to leave open access to radiation beams from a treatment machine to most of the front and to the sides of the patient's head and neck and upper torso. Also shown is a camera system 110 comprising one or more cameras 111, 112, and 113. These may be standard optical video cameras, they may be infrared filtered cameras, they may be linear cameras either infrared or non-infrared which view the treatment couch and patient region. They can index the orientation of the patient's head H relative to the neck N or torso T in a variety of ways. In this FIG. 11 are shown index points such as 104, 105, 106, 107, and 108 which can be placed at various points on the patient's body and can be viewed by the cameras indicated by the dashed lines such as 120 to schematically indicate viewing paths (not all shown). By optical processing, which is standard in neurosurgery (see the OTS System by Radionics, Inc., Burlington, Mass.), the positions of these index spots can be tracked by an optical image processor 114. The optical processor can process video or linear camera information. It will then be a representation of the orientation and configuration of the patient's head, neck, and torso, as well as position external apparatus such as clamping apparatus illustrated by over-arm 5. The index points, such as 104, can be LED emitters, reflectors of light, or can be illuminated and viewed by passive illumination. CT image information or other historic information such as a previous set-up of the patient on a couch can be inputted (block 115), and a comparator 116 can be made to determine if the patient is in the correct repeat positioning on the couch 8. At the same time, a treatment planning computer 118 could be invoked using CT or MR data to determine internal targets in the body and beam configuration, which also can be coordinated in comparator 116 to determine the relative position according to the light signals from 114 and other preplanned data from 115. Element 117 may be a controlled or a planning computer as well which can determine the relative position of the treatment couch relative to external beams or radiation so as to orient the patient's body or move the couch to an appropriate position or to govern beams and their focal point to irradiate internal targets within the body. Also shown are light emitters 121 on the treatment couch which could be used in conjunction with the camera set 110 to determine where the patient's body is relative to an external treatment machine schematically indicated by 122 (such as a LINAC), which also may have optical emitters or reflectors 123 placed in patterns on it to give the appropriate orientation relative to the patient and to the couch 8. Thus, the camera system may coordinate the treatment machine, the beams from it, the target position, the repeat location of the patient, and the immobilization integrity via the system shown in FIG. 11. In this way, for example, the beam of X-rays from a LINAC 124, as they converge on the patient, can be controlled and monitored to be sure they are aimed and guided to the appropriate position in the patient's body according to the treatment plan and to the tracking system 110. In the example of FIG. 11, the camera system in conjugation with the fiducial markers such as 105 and the patient immobilizer 11 may comprise a referencing system for the patient on the imaging or treatment couch. For repeat positioning, this same or similar system can be used during radiation treatment so as to place the patient at the appropriate point and relative orientation, as in previous scanning.

As will be apparent to those skilled in the art, the system of process described above may take many forms with a multitude of variations. A variety of methods of immobilizing, restraining and indexing the patient's head with respect to his neck and upper torso can be devised. Mechanical, laser, video, camera, or X-ray camera registration for this purpose may be invoked. Various geometries of immobilizers and restrainers may be employed, examples of which are molds, casts, bite pieces, etc. Variation in process steps can be used to proceed with repeat localization and initial localization on CT/treatment couches or other configurations and treatment machines such as seats, stand-up positions, etc.

In view of these considerations, and as will be appreciated by persons skilled in the art, implementations and systems should be considered broadly and with reference to the claims as set forth below.

What is claimed is:

1. A system for locating repeatedly a head of a patient and a neck or torso of said patient, comprising:
    a. a head immobilizer to immobilize said head in a head position; and,
    b. a reference structure to determine a relative position of said neck or torso with respect to said head position, whereby said head can be repeatedly placed in said head position, and said neck or torso can be repeatedly placed in said relative position.

2. The system of claim 1 wherein said head immobilizer comprises a dental impression of teeth of said patient.

3. The system of claim 1 wherein said head immobilizer comprises a mold of an exterior portion of said head of said patient.

4. The system of claim 1 wherein said reference structure comprises a frame that can be attached to said head immobilizer in a determined position with respect to said head position, and having an indexing gauge to determine the position of said neck or torso with respect to said frame.

5. The system of claim 4 wherein said frame comprises at least one depth probe hole through which a depth probe can be passed to determine the distance of said frame to said neck or torso of said patient.

6. The system of claim 1 wherein said reference structure comprises at least one laser beam which can be directed at a known point on said head when placed in said head position, and can be directed at a known point on said neck or torso.

7. The system of claim 1 and further comprising an adjustment positioner to adjust the position of said head with respect to said neck or torso to bring said neck or torso into said relative position with respect to said head position repeatedly.

8. The system of claim 7 wherein said adjustment positioner comprises translation and/or rotation positioning structures to translate or rotate said head with respect to said neck or torso.

9. The system of claim 1 wherein said head immobilizer comprises a couch head immobilizer to immobilize said head in said head position with respect to a couch of a scanner/treatment apparatus, and said reference structure enables repeat positioning of said neck or torso in said relative position with respect to said head position.

10. The system of claim 9 wherein said scanner/treatment apparatus is a CT scanner and wherein said reference structure comprises graphic reference structures to develop image data from a CT scan of said head or said neck or torso to relate the positions of anatomical structures of said head and said neck or torso to the position of said reference structure.

11. The apparatus of claim 9 wherein said scanner/treatment apparatus is a radiation therapy apparatus producing beams of radiation, and said reference structure comprises beam guidance structures to guide said beams to targets within said head and/or said neck or torso according to a treatment plan.

12. The system of claim 9, 10, or 11 wherein said head immobilizer comprises an over-arm that is positioned over said head and in immobilizing contact with said head and wherein said head immobilizer is configured to provide open access to the sides of the head.

13. The system of claim 1 and further comprising a head or torso adjustment positioner to adjust the position of said neck or torso with respect to said head position to bring said neck or torso into said relative position with respect to said head position repeatedly.

14. The system of claim 1 further comprising:
a shoulder immobilizer to immobilize shoulders of said patient and therefore to immobilize said neck or torso of said patient with respect to said head.

15. The system of claim 14 wherein said reference structure is a mechanical frame having a gauge that provides positional data of said mechanical frame with respect to said head and with respect to said neck or torso, whereby said positional data can be used to repeatedly establish said relative position.

16. The system of claim 15 wherein said mechanical frame defines at least one depth probe hole through which a depth probe can be passed to determine the position of said mechanical frame to at least one point on said body.

17. The system of claim 14 wherein said reference structure comprises at least one laser beam which can be directed toward at least one known point on said body.

18. The system of claim 14 wherein said head immobilizer and said shoulder immobilizer comprise a mold of said head and said neck or torso.

* * * * *